United States Patent
Emanuel

(10) Patent No.: US 7,336,689 B2
(45) Date of Patent: *Feb. 26, 2008

(54) EFFICIENT METHOD AND APPARATUS FOR GENERATING SINGLET DELTA OXYGEN AT AN ELEVATED PRESSURE

(75) Inventor: George Emanuel, Arlington, TX (US)

(73) Assignee: KSY Corporation, Arlington, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 11/516,161

(22) Filed: Sep. 6, 2006

(65) Prior Publication Data

US 2007/0009004 A1    Jan. 11, 2007

Related U.S. Application Data

(63) Continuation of application No. 10/453,148, filed on Jun. 3, 2003, now Pat. No. 7,116,696.

(60) Provisional application No. 60/387,539, filed on Jun. 10, 2002.

(51) Int. Cl.
*H01S 3/095* (2006.01)
*C01B 13/00* (2006.01)

(52) U.S. Cl. ........................ 372/89; 423/579
(58) Field of Classification Search ................. 372/89; 423/579
See application file for complete search history.

(56) References Cited

U.S. PATENT DOCUMENTS

| 4,407,282 A | 10/1983 | Swartz et al. |
| 4,461,756 A * | 7/1984 | Rockenfeller ............ 423/579 |
| 4,640,782 A | 2/1987 | Burleson et al. |
| 5,607,924 A | 3/1997 | Magda et al. |
| 5,974,072 A * | 10/1999 | Hartlove et al. .............. 372/89 |
| 6,072,820 A | 6/2000 | Dickerson |
| 6,630,105 B1 | 10/2003 | O'Neill et al. |
| 7,116,696 B2 * | 10/2006 | Emanuel ..................... 372/89 |

FOREIGN PATENT DOCUMENTS

WO    WO 03/104145 A1    12/2003

OTHER PUBLICATIONS

Alfano, A.J. and Christe, K.O., "Singlet Delta Oxygen Production from a Gas-Solid Reaction," Angew. Chem. Int. Ed. 41, No. 17, pp. 3252-3254 (2002).
Rybalkin, V. et al., "Nearly attaining the theoretical efficiency of supersonic chemical oxygen-iodine lasers," Applied Physics Letters, vol. 85, No. 24, pp. 5851-5853 (Dec. 13, 2004).
Endo, M., et al., "Development of Hybrid Simulation for Supersonic Chemical Oxygen-Iodine Laser," AIAA Journal, vol. 45, No. 1, pp. 90-97 (Jan. 2007).

* cited by examiner

*Primary Examiner*—Armando Rodriguez
(74) *Attorney, Agent, or Firm*—Paul V. Storm; John J. Patti; Storm LLP

(57) ABSTRACT

An improved singlet delta oxygen generator (SOG) and method of its use are disclosed. The improved SOG is compact and scalable, capable of operating in a zero-gravity or low gravity environment, requires no gaseous diluent or buffer gas, and is capable of operating at pressures as high as one atmosphere. The improved SOG also efficiently utilizes the reactants and produces a $O_2(^1\Delta)$ stream that is largely free of chlorine and water vapor contamination and therefore does not require a BHP regeneration system or a water vapor trap. When used as part of a COIL system, the SOG may be part of a plenum that directly feeds the laser's nozzle. The close proximity of the SOG to the laser cavity allows operation of the SOG at higher pressures without significant depletion of available $O_2(^1\Delta)$ through collisional deactivation.

14 Claims, 3 Drawing Sheets

EFFICIENT METHOD AND APPARATUS FOR GENERATING SINGLET DELTA OXYGEN AT AN ELEVATED PRESSURE

CROSS REFERENCE TO RELATED APPLICATIONS

This application is a continuation of U.S. patent application Ser. No. 10/453,148, entitled "EFFICIENT METHOD AND APPARATUS FOR GENERATING SINGLET DELTA OXYGEN AT AN ELEVATED PRESSURE" filed on Jun. 3, 2003 now U.S. Pat. No. 7,116,696, which claims priority to U.S. Provisional Application Ser. No. 60/387,539, filed on Jun. 10, 2002.

TECHNICAL FIELD

The present invention relates generally to an improved method and apparatus for generating electronically excited states of oxygen with increased efficiency and at an elevated pressure.

BACKGROUND OF THE INVENTION

The invention relates to an improved method and apparatus for generating the singlet delta electronically excited state of diatomic oxygen, $O_2(a^1\Delta_g)$, in vapor form. The apparatus for generating singlet delta oxygen is referred to as a singlet oxygen generator or SOG. Singlet delta oxygen is most typically used in chemical lasers, or specifically in chemical oxygen-iodine lasers (COIL), although there may be other uses for singlet delta oxygen and particularly for singlet delta oxygen generated according to the method and using the SOG of the invention.

Singlet delta oxygen is generally produced by reacting aqueous basic hydrogen peroxide (BHP) with chlorine. Aqueous BHP is produced by mixing liquid water with an aqueous solution of hydrogen peroxide ($H_2O_2$) and an aqueous solution of potassium hydroxide (KOH). Alternatively, sodium hydroxide (NaOH) may be used in place of KOH. In the BHP solution, the $H_2O_2$ and KOH exist as various ionic molecules. The mixing and reactive process in making BHP is exothermic.

When BHP is mixed with chlorine, the following stoichiometric chemical reaction takes place:

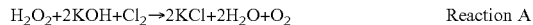

$$H_2O_2 + 2KOH + Cl_2 \rightarrow 2KCl + 2H_2O + O_2 \qquad \text{Reaction A}$$

where the oxygen is in its lowest energy electronically excited state, $O_2(a^1\Delta_g)$. For convenience, this is referred to as singlet delta oxygen or as $O_2(^1\Delta)$. Normally, oxygen is in its electronic ground state, $O_2(X^3\Sigma_g^-)$, which, hereafter, is written as $O_2(^3\Sigma)$ or just $O_2$. In Reaction A, the chlorine vapor diffuses into the aqueous BHP solution, forming potassium chloride (KCl), or sodium chloride (NaCl) if NaOH is used in the reaction, water, and $O_2(^1\Delta)$. The $O_2(^1\Delta)$ can form bubbles and diffuse out of the solution. The presence of singlet delta oxygen from the reaction of BHP and chlorine in Reaction A is evident by a red dimol emission (see "Direct Spectroscopic Evidence for a Deuterium Solvent Effect on the Lifetime of Singlet Delta Oxygen in Water," Kajiwara and Kearns, *Journal of the American Chemical Society*, vol. 95, No. 18, pp. 5886-5890, September 1973) that is visible by sight. This emission stems from the chemiluminescence of $(O_2(a^1\Delta))_2$.

Singlet delta oxygen has a long radiative lifetime of about 90 minutes, but can collisionally deactivate in much less time, resulting in the production of the ground state and the next higher electronically excited state, $O_2(^1\Sigma)$, of diatomic oxygen. An important process is the gas-phase pooling reaction:

$$O_2(^1\Delta) + O_2(^1\Delta) \leftrightarrow O_2(^3\Sigma) + O_2(^1\Sigma) \qquad \text{Reaction B}$$

wherein $O_2(^1\Sigma)$ is shorthand for $O_2(b^1\Sigma_g^+)$, which is a more energetic electronic state than singlet delta oxygen. The $O_2(^1\Sigma)$ and $O_2(^3\Sigma)$ are contaminants or byproducts in the singlet delta oxygen stream, which reduce the yield of singlet delta oxygen. When $O_2(^1\Delta)$ is the preferred product, as is the case with the chemical laser, then Reaction B is a deactivation process to the extent that the forward rate exceeds the backward rate.

Reaction B is a gas-phase process that can be viewed as producing the $O_2(^1\Sigma)$ state. In non-laser applications, this state may be preferred as equal to or superior to the $O_2(^1\Delta)$ state. Hereafter, when discussing the singlet delta state of oxygen, as generated by an SOG according to the invention, the $O_2(^1\Sigma)$ state, produced by Reaction B, is not excluded.

An important deactivation process is the dimol reaction:

$$O_2(^1\Delta) + O_2(^1\Delta) \rightarrow (O_2(a^1\Delta))_2 \qquad \text{Reaction C}$$

Reactions B and C are the primary deactivation process for removing $O_2(^1\Delta)$ in the gas phase. The gas phase generated by the SOG of this invention consists of $O_2(^1\Delta)$ (which is the preferred species for COIL), $O_2(^3\Sigma)$, $O_2(^1\Sigma)$, $H_2O$, and possibly a small mole fraction of chlorine vapor. The $O_2(^3\Sigma)$, $O_2(^1\Sigma)$, $H_2O$ and chlorine vapor (if any) are referred to as the gas-phase byproducts. In addition, there may or may not be added diluent, which is not a byproduct. For COIL, a common measure of effectiveness is the yield, which is the mole ratio of $O_2(^1\Delta)$ divided by the total oxygen.

Various types of singlet delta oxygen generators have been developed in the prior art. These generators typically use BHP with chlorine and a diluent gas, such as helium. Optimum singlet delta oxygen production occurs when the $H_2O_2$ molar flow rate, relative to the KOH, or NaOH, molar flow rate is about double that suggested by Reaction A; i.e., $H_2O_2$ and KOH have approximately the same molar flow rate. These molar flow rates were used in the feasibility experiment according to the invention, as described later.

One type of prior art SOG uses a transverse flow uniform droplet method in which BHP droplets, ranging in size from 0.4 mm to 0.5 mm (15.8 mil to 19.7 mil) diameter, fall under the influence of gravity into a sump. Chlorine vapor and a diluent gas flow across the path of the droplets. The flow speed of the chlorine vapor and diluent is limited, otherwise the droplets would be transported downstream with the diluent and the generated oxygen. There is an adverse trade-off in that the maximum vapor speed, which includes the generated singlet delta oxygen, must decrease as the droplet size decreases. Generator pressures of around 92 Torr (0.12 atm), most of which is due to helium diluent, have been reported in this type of SOG. The partial pressure of the generated oxygen reported for this type of SOG is only around 14.3 Torr (0.02 atm).

Another type of prior art SOG is a verticoil oxygen generator. In this device, a number of disks rotate such that the lower portion of the disks is in a BHP sump. The upper portion of the disks is thus wetted with a BHP film. Chlorine vapor and diluent flow past the upper part of the disks to react with the BHP film. Generator pressures of about 40 Torr (0.05 atm), most of which stems from the helium diluent that enters the reactor with the chlorine vapor, have been reported in this type of SOG.

Another type of prior art SOG is a twisted-flow aersol-jet singlet oxygen generator. A partial pressure of about 75 Torr (0.1 atm) of singlet delta oxygen has been reported for this type of generator, but this $O_2(^1\Delta)$ pressure decreases, to around 22.5 Torr (0.03 atm), at a nozzle inlet for a laser. This significantly decreases the laser efficiency.

The foregoing prior art SOGs have, in common, a number of adverse characteristics:
  (a) The devices are bulky, and typically require ducting to transport the $O_2(^1\Delta)$ stream to the nozzle that feeds the laser cavity. These devices are not well suited for scaling a laser module to a high-power level.
  (b) Primarily, because of Reactions B and C, the singlet delta oxygen partial pressure entering the inlet of the laser's nozzle has not exceeded about 22.5 Torr (0.03 atm) in prior art systems. To increase the plenum pressure of the laser's nozzle, a diluent gas is used, typically helium or nitrogen. The need for supply tanks, plumbing, etc., to accommodate the use of a diluent gas further increases the size and weight of the overall system.
  (c) The devices have difficulty keeping water vapor and water droplets from being entrained in the singlet delta oxygen stream. Water vapor is a deactivator that reduces the laser's performance. In many prior art systems, a water vapor trap and liquid separator, located between the SOG and laser nozzle, are needed. These traps, however, reduce the singlet delta oxygen concentration that enters into the laser's nozzle.
  (d) Only a small percentage of the reactive chemicals in the BHP solution are utilized as the BHP flows through the oxygen generator. This results in a large and heavy BHP feed system, or a large and heavy system to recondition or regenerate the partly spent BHP.
  (e) As described in "Mixed Marks for the ABL," by Canan in *Aerospace America*, pp. 38-43, August 1999, Earth's gravitational field is required to provide buoyancy for separating the oxygen vapor from the liquid. Prior art SOG devices that rely on gravity for separation of singlet delta oxygen from the reactant flow, or that rely on gravity for reactant flow, such as the BHP droplets which fall by force of gravity in a transverse flow uniform droplet SOG, are not suitable for operation in a space environment.
  (f) Prior art systems do not appear to yield a chemical efficiency for the laser above about 30%.

In addition to prior art SOGs, gas sparger devices are relevant to the production of singlet delta oxygen according to the invention and as discussed more fully below. Gas sparger devices are designed to remove volatile contaminants from a liquid. In a prior art gas sparger, a contaminated liquid is injected, under pressure, onto the inside surface of a porous tube with a circular cross section. Centrifugal force keeps the liquid attached to the inside of the porous walled tube. The liquid follows a helical path as it makes a number of revolutions along the wall. Air, under pressure, is injected from the outside surface of the porous walled tube, through the tube, after which it mixes with the liquid. Most of the volatile contaminants are entrained with the air, which separates from the liquid, due to buoyancy that stems from the centrifugal force. Chemical reactions do not occur in typical gas spargers.

SUMMARY OF THE INVENTION

The present invention provides an improved method and apparatus for generating singlet delta oxygen. This invention is preferably used to generate singlet delta oxygen for use in chemical lasers, but there may be other uses for the singlet delta and singlet sigma electronically excited states of oxygen. As in prior art systems, production of $O_2(^1\Delta)$ is achieved through the reaction of BHP and chlorine in a SOG according to the invention. A dilute basic hydrogen peroxide, or BHP, solution is produced according to the invention by mixing aqueous hydrogen peroxide, water, and aqueous potassium hydroxide, or alternatively sodium hydroxide or a mixture of several hydroxide compounds. The BHP production process is exothermic; therefore, the solution is preferably cooled during preparation and afterward.

Cooled BHP is then injected, under pressure typically greater than 400 Torr, and preferably greater than about 600 Torr, into a SOG reaction chamber with a concave curved wall. At the point of entry, the solution is a thin, high-speed, liquid layer that flows over the concave wall. The high speed of injection results in a centrifugal force that prevents the aqueous solution from separating from the concave wall. Shortly after the start of the concave wall, chlorine vapor is injected, under pressure sufficient to choke the chlorine vapor flow (i.e. it approaches becoming sonic) in the porous wall and to provide sufficient chlorine for its reaction with BHP. The chlorine is preferably injected through a porous wall that is a small section of the concave wall. Alternatively, the chlorine may be injected under pressure through a converging, two-dimensional nozzle that terminates in a thin slit located in the plane of the concave wall. The injected chlorine vapor, in the form of small bubbles, rapidly mixes and reacts with the BHP solution while the flow is still passing over the concave wall. The reaction with the chlorine produces singlet delta oxygen in a liquid, or frothy, layer.

The singlet delta oxygen forms vapor bubbles. Because of their low density relative to the liquid solution, the bubbles experience a significant pressure gradient that is transverse to the concave wall. This gradient, which is associated with the aforementioned centrifugal force, causes the vapor bubbles to depart the aqueous solution on the side of the liquid, or frothy, layer opposite from where the chlorine vapor enters. Thus, there is little, if any, chlorine contamination in the $O_2(^1\Delta)$ stream. As soon as most, or all, of the generated $O_2(^1\Delta)$ has departed the BHP solution, the spent solution is removed from the reaction chamber by means of an outlet or exhaust duct for the liquid.

The molar flow rate of the chlorine is adjusted to maximally utilize the BHP solution with little, if any, chlorine entrained in the oxygen vapor stream. Hence, the concentrations of the active ions and molecules in the BHP solution are significantly depleted. A BHP regenerator system is thus unnecessary.

The salt generated by the BHP-chlorine reaction remains dissolved in the highly dilute aqueous solution. The high-speed aqueous solution passes through the reaction chamber very quickly. Inside the reaction chamber, the temperature of the liquid increases due to exothermic reactions with the chlorine. Because the BHP solution contains added water and is cooled before it enters the reaction chamber, the magnitude of the temperature increase in the reaction chamber is minimized. This factor, in combination with the reduction of the vapor pressure of the water by the solute, and the few milliseconds that the high-speed solution is located inside the reaction chamber, results in a low contamination level of the $O_2(^1\Delta)$ gas with water vapor.

These preferred features may be used singularly or combined for the efficient generation of $O_2(^1\Delta)$ in a SOG that has a number of advantages over the prior art, particularly when used as a source of $O_2(^1\Delta)$ for a chemical oxygen iodine laser. One of these is scalability. Scalability is being able to extend by an arbitrary amount a single laser module in the direction of the laser beam that circulates inside the laser cavity. These advantages thus include: (1) the SOG is compact and scalable (2) it can operate in a zero-gravity or near zero gravity environment such as on a space satellite, (3) no added diluent or buffer gas is needed, (4) the $O_2(^1\Delta)$ may be generated at an elevated pressure, (5) the hydroxide and $Cl_2$ chemicals are efficiently utilized, with high percentages of utilization, up to 100% for both, based on the known fast reaction rates, (6) the $O_2(^1\Delta)$ stream is largely free of chlorine and water vapor contamination, and (7) the $O_2(^1\Delta)$ yield at the laser nozzle throat is well above prior art systems and may be greater than 70%.

BRIEF DESCRIPTION OF THE DRAWINGS

The accompanying drawings are incorporated into and form a part of the specification to assist in explaining the present invention. The drawings are intended for illustrative purposes only and are not intended as exact representations of the embodiments of the present invention. The drawings further illustrate preferred examples of how the invention can be made and used and are not to be construed as limiting the invention to only those examples illustrated and described. In these drawings, the same reference characters are used throughout the views to indicate like or corresponding parts. The various advantages and features of the present invention will be apparent from a consideration of the drawings in which.

DETAILED DESCRIPTION

Figure 1:
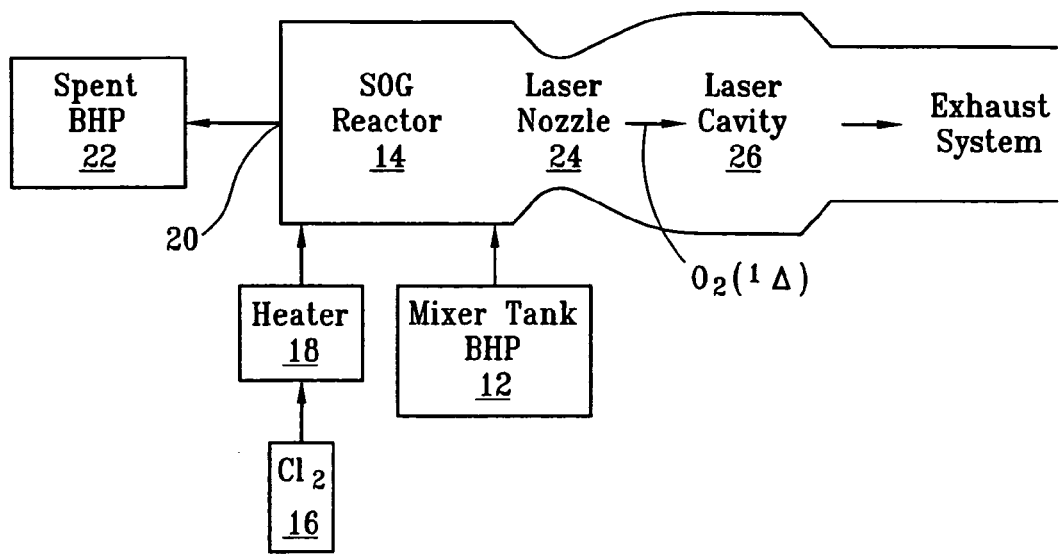
FIG. 1 is a schematic diagram of a SOG system, including BHP and chlorine feed systems, as part of a plenum feeding a laser nozzle according to one aspect of the invention.

The following describes the preferred embodiment of a SOG system and its method of use according to the present invention and according to a feasibility experiment for the present invention by reference to FIGS. 1-4. Although the preferred embodiment and a feasibility experiment for the present invention are described, the description is not intended to limit the scope of the invention as defined by the claims. Some details of the SOG and chemical supply systems and their methods of use, including various gauges, fittings, piping, etc. are well known in the art, and as such are neither shown nor described. Even though numerous characteristics and advantages of the present invention are shown and described in the drawings and accompanying text, the description is illustrative only, and changes may be made, especially in matters of arrangement, shape and size of the parts, within the scope of the invention to the full extent indicated by the broad general meaning of the terms used in the claims.

FIG. 1 is a schematic diagram of a SOG system, including BHP and chlorine feed systems, as part of a plenum wall feeding a (COIL) laser nozzle according to one aspect of the invention. The iodine feed and injection systems for the COIL are not depicted in FIG. 1. The first step in the overall process is the mixing of liquid water, aqueous $H_2O_2$ and aqueous KOH in mixer tank 12. Sodium hydroxide or a mixture of several hydroxide compounds may be used in place of potassium hydroxide. The resulting mixture is referred to as a basic hydrogen peroxide (BHP) solution.

In prior art systems, the $H_2O_2$ molar flow rate, relative to the KOH, or NaOH, molar flow rate is about double that suggested by Reaction A, i.e., $H_2O_2$ and KOH have approximately the same molar flow rate. Preferably, according to the invention, the $H_2O_2$ molar flow rate is about 50% or more of the KOH molar flow rate, and most preferably between 50% to 110% of the KOH molar flow rate. The aqueous KOH and aqueous $H_2O_2$ mixed in mixer tank 12 are commercially available aqueous solutions that are each buffered with additional water. Due to this additional water, the BHP solution is more dilute than is used in prior art systems. Although not necessarily optimum values, the mole ratios of $H_2O_2$, KOH, and $H_2O$ used in the feasibility experiment discussed below were approximately 1:1:10, where the $H_2O$ molar value of 10 consists of the aqueous portions of the $H_2O_2$ and KOH solutions plus the added water. In the discussion of molar ratios of $H_2O$, $H_2O_2$, and KOH herein, the $H_2O$ value consists of the aqueous portions of the $H_2O_2$ and KOH solutions plus added $H_2O$. The amount of dilution is higher than prior art practice and may be further increased according to the invention to produce a highly dilute BHP solution to aid in reaction temperature reduction.

The aqueous KOH, aqueous $H_2O_2$, and added water require cooling when they are mixed because of the exothermicity of reactions. Once mixed, and sometime before usage, the BHP should be cooled to a temperature just above its freezing point, preferably to a temperature 1° C. to 10° C. above its freezing point. This temperature is below the freezing point for pure liquid water, since a solute lowers the freezing point. The BHP enters SOG Reactor 14 at a temperature where its water vapor partial pressure is below the 4.6 Torr (0.006 atm) value of pure water at 0° C. Due to the use of a relatively dilute BHP solution according to the preferred embodiment of the invention, problems in the prior art with anomalous freezing of the BHP are not encountered.

Chlorine liquid from chlorine supply tank 16 is vaporized in a heater 18 with the chlorine vapor flowing into SOG 14. A pump is usually not required, since the room temperature vapor pressure of liquid chlorine should be sufficient for providing the desired flow rate of chlorine to SOG 14.

The molar flow rate of the chlorine is readily adjusted to maximally utilize the BHP solution by significantly depleting the concentrations of active ions and molecules in the BHP solution. The molar flow rate of chlorine is preferably slightly less than that of the KOH or NaOH. Preferably, the chlorine molar flow rate is about 80% to about 95% of the KOH or NaOH molar flow rate, and most preferably about 90% to about 95% or more of the KOH or NaOH molar flow rate. These molar flow rates result in nearly 100% utilization of the KOH (or NaOH) and chlorine. Due to the efficient utilization of the reactants, a BHP regeneration or recycling system is not necessary according to the invention.

SOG 14 preferably includes a concave curved wall over which the BHP and chlorine are injected and react to produce singlet delta oxygen. After the reaction, spent BHP solution, comprising salts, small amounts of KOH or NaOH based ions and excess $H_2O_2$, exits SOG 14 through exhaust outlet 20 to a collection tank 22 for proper disposal. Due to the efficient utilization of chemicals according to the invention, it is not necessary to recycle or regenerate the spent BHP solution after the reaction in SOG 14. Preferably, 90% or more of the BHP solution entering SOG 14 comprises non-recycled $H_2O_2$ and hydroxide compounds and most preferably the BHP solution comprises entirely new, non-recycled $H_2O_2$ and hydroxide compounds. Non-recycled refers to chemicals or compounds that have not been recycled from the spent solution exiting SOG 14 through outlet 20. Materials recycled from other processes may be used according to the invention.

SOG 14 is preferably part of a plenum feeding a laser nozzle 24 when SOG is used to produce $O_2(^1\Delta)$ for a COIL. A $O_2(^1\Delta)$ stream exits SOG 14 through nozzle 24 to feed a laser cavity 26. Iodine feed and injection systems for the COIL are not shown in FIG. 1.

Figure 2:
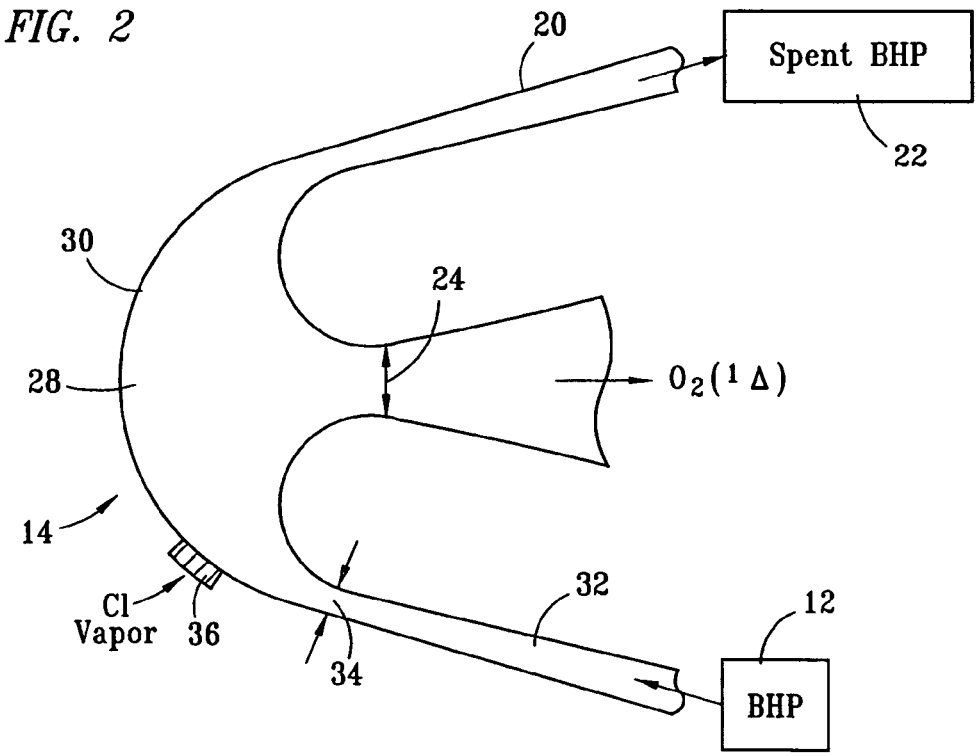
FIG. 2 is a cross-sectional side view of a SOG as part of a plenum feeding a laser nozzle according to one aspect of the invention.

FIG. 2 is a cross-sectional side view of a SOG 14 as part of a plenum wall feeding a laser nozzle 24 according to one aspect of the invention. The iodine feed and injection systems for the laser are not depicted in FIG. 2. BHP and chlorine feed systems are also not depicted in FIG. 2. SOG 14 includes a reaction chamber 28 with a concave curved wall 30. A nominal radius of curvature for concave wall 30 is 2.5 cm (1 inch). SOG 14 is a two-dimensional flow apparatus, the dimension of which with respect to the plane of FIG. 2 is arbitrary. Thus, the preferred embodiment of the SOG 14 is compact and fully scalable.

BHP from mixer 12 enters reaction chamber 28 under pressure through a converging nozzle 32 and exits the nozzle at its throat 34 at a considerable speed, typically in excess of 15 m/s (49.2 ft/s). The BHP solution travels along concave wall 30 and remains in substantial contact with this wall. At the point of entry, the BHP solution is a thin, high-speed, liquid layer that may develop into a frothy layer along concave wall 30. It is estimated that the thickness of the liquid layer is less than about 4 mm (0.16 inches), with the frothy layer being about 2 to 4 times thicker than the liquid layer. It is preferred that the fluid layer along concave wall 30 have a thickness of 15 mm (0.6 in) or less. The solution remains a thin layer as it flows over concave wall 30. The high speed of injection results in a centrifugal force that prevents the aqueous solution from substantially separating from the concave wall 30. The centrifugal force is quite large since the BHP is a liquid, the flow speed is large and the radius of curvature of concave wall 30 is small.

Chlorine vapor is preferably injected under pressure through a porous wall 36 that is a part of concave wall 30. The chlorine injection process is regulated to avoid separating the liquid layer from the concave wall. Alternatively, chlorine can be injected through a converging nozzle with a throat located downstream of BHP nozzle throat 34, as used in the feasibility experiment described below.

Porous wall 36 is located downstream of BHP nozzle throat 34. Most preferably, porous wall 36 is made from a sintered metal, such as Nickel 200, or other materials, or porous plastic. It is also preferred that the chlorine flow through porous wall 36 chokes at the exit surface of the wall 36 on the interior of reaction chamber 28. A choked flow ensures a nearly uniform distribution of chlorine vapor over the exit surface of porous wall 36. It also provides useful momentum for the chlorine that will aid both the chlorine/BHP mixing and the subsequent removal of the singlet delta oxygen from the solution. Choking also enables better control of the chlorine molar flow rate. The magnitude of the chlorine molar flow rate, which is preferably slightly less than the molar flow rate of KOH or NaOH, establishes the magnitude of the surface area of porous wall 36 as will be understood by those of skill in the art.

The pressure of the chlorine at the exit surface of porous wall 36 must be approximately equal to that of the BHP flowing along concave wall 30. Due to the centrifugal force along concave wall 30, the BHP pressure at the wall exceeds that in a plenum. To match the BHP wall pressure, the chlorine vapor first goes through an expansion as the flow adjusts from the constricted flow area inside the porous wall 36 to the external surface of the porous wall inside reaction chamber 28. This expansion occurs over a distance of about one average pore diameter, which can be as small as 0.2 µm (0.008 mil) or as large as 100 µm (4 mil) or larger. Before the flow exits the porous wall 36, it may go through a compression whose downstream pressure matches or approximates the BHP wall pressure. The injected chlorine vapor, in the form of small bubbles, rapidly mixes and reacts with the BHP solution while the flow is still passing over the concave wall. The chlorine vapor bubbles are approximately the same size as the pores in porous wall 36. The chlorine bubbles are subjected to a large shearing force as they enter the high-speed BHP layer. The shearing force distorts the chlorine bubbles and helps result in a large contact surface area. The liquid-gas contact surface area according to the invention is significantly higher than in prior art SOG devices. The chlorine and BHP react and produce $O_2(^1\Delta)$ in the liquid, or frothy, layer. According to the invention, it is not necessary to add any diluents, such as helium, to SOG 14, although diluents may be added.

The singlet delta oxygen forms vapor bubbles. Because of their low density relative to the liquid solution, the bubbles experience a significant pressure gradient, or buoyancy force associated with the centrifugal force of flow along concave wall 30, that is transverse to concave wall 30. This buoyancy force causes the low-density vapor bubbles to depart the aqueous solution on the side of the liquid, or frothy, layer opposite from where the chlorine vapor enters through porous wall 36. The centrifugal force also permits SOG 14 to operate in a zero-gravity or low gravity environment. This arrangement in combination with the high percentage utilization of up to 100% or nearly 100% of the chlorine in the BHP-chlorine reaction, results in little, if any, chlorine contamination of the $O_2(^1\Delta)$ stream. The $O_2(^1\Delta)$ stream departs SOG reaction chamber 28 through laser nozzle throat 24. A small percentage may leave through an outlet or exhaust duct. The laser nozzle is preferably a converging/diverging supersonic nozzle including a means for injecting iodine into the $O_2(^1\Delta)$, such as that described in U.S. Patent Application Ser. No. 60/410,857 filed by Applicant on Sep. 13, 2002. Iodine feed and injections systems are not depicted in FIGS. 1-2.

Many factors control the rate at which the $O_2(^1\Delta)$ departs the liquid solution to exit through nozzle throat 24. As the reactants pass through SOG 14 very quickly, it is important that the $O_2(^1\Delta)$ depart the liquid solution quickly so that it does not remain entrained in the solution as the solution is exhausted to the collection tank 22. These factors include the injected thickness of the BHP layer, the injection speed of the BHP, the average pore size in porous wall 36, the radius of curvature of concave wall 30, which is nominally around 2.5 cm (1 in), the angular extent of concave wall 30, which is preferably less than 160° in extent, and the pressure inside reaction chamber 28. These factors are chosen iteratively, in conjunction with other design and performance constraints as will be understood by those of ordinary skill in the art. For instance, sintered metal porous sheets are available in a range of thicknesses with a range of average pore sizes. As the average pore size decreases, the pressure change, for a given flow rate of chlorine, across the porous wall increases.

As soon as most, or all, of the generated $O_2(^1\Delta)$ has departed the BHP solution, the spent solution is removed from reaction chamber 28 by means of an exhaust duct or outlet 20. The spent solution is comprised of salt byproducts (KCl or NaCl), a small quantity of KOH or NaOH based ions and excess $H_2O_2$. It is preferred to remove the spent solution as quickly as possible with a smooth inlet for exhaust duct 20 that avoids splashing or aerosol formation that could contaminate the $O_2(^1\Delta)$ vapor stream. A suction pump in the exhaust may be used, if necessary, to assist with removal of the spent solution. The spent solution is stored in collection tank 22 for proper disposal; no BHP regeneration or recycling system is needed according to the invention.

The salt generated by the BHP-chlorine reaction remains dissolved in the highly dilute aqueous solution. The high-speed aqueous solution passes through reaction chamber 28 very quickly, preferably in fewer than about 20 milliseconds, more preferably in fewer than about 10 milliseconds, and most preferably in fewer than about 5 milliseconds. Inside reaction chamber 28, the temperature of the liquid increases due to exothermic reactions with the chlorine. Because the BHP solution contains added water and is cooled before it enters the reaction chamber, the magnitude of the temperature in the reaction chamber is minimized. A finite amount of time is required for the water vapor partial pressure to reach its equilibrium value with the post-reaction temperature of the aqueous solution. As the reactants pass through reaction chamber 28 very quickly, there is insufficient time for the evaporation of liquid water to establish an equilibrium value for the water vapor at the post-reaction temperature, in the singlet delta oxygen exhaust stream. This factor, in combination with the reduction of the vapor pressure of the water by the solute, and the few milliseconds that the high-speed solution is located inside the reaction chamber, results in a low contamination level of the $O_2(^1\Delta)$ gas stream with water vapor. According to the invention, it is not necessary to use a water vapor trap prior to laser nozzle 24; however, a water vapor trap may be used if desired.

Preferably, the $O_2(^1\Delta)$ stream is substantially free of any contaminants, such as water vapor and chlorine vapor byproducts, at the inlet of the laser nozzle without any further processing, such as a water vapor trap, between the time the $O_2(^1\Delta)$ exits the reactant solution and enters the nozzle inlet. At the nozzle inlet, the $O_2(^1\Delta)$ stream preferably comprises about 70% yield or greater singlet delta oxygen, and more preferably comprises about 85% or greater, and most preferably comprises about 90% or greater singlet delta oxygen. Additionally, without having passed the $O_2(^1\Delta)$ stream through a water vapor trap, the $O_2(^1\Delta)$ stream preferably comprises less than about 15% water vapor at the nozzle inlet, and more preferably comprises less than about 10% water vapor at the nozzle inlet, and most preferably comprises less than about 5% water vapor at the nozzle inlet.

The pressure in reaction chamber 28 refers to the gaseous pressure of the $O_2(^1\Delta)$ plus the gas-phase byproducts, i.e., the total pressure. It would also include the pressure of diluent; in this invention diluent is not utilized, although it could be. Of the byproducts in chamber 28, the mole fraction of $H_2O$ and $Cl_2$ is small. The amount of $O_2(^3\Sigma)$ and $O_2(^1\Sigma)$ depends on the yield. With a high yield, say 85% or more, the bulk of the gas is $O_2(^1\Delta)$.

The pressure in reaction chamber 28 may be as high as about 760 Torr (1 atmosphere), or even up to about 910 Torr (1.2 atm) or higher, without the addition of any diluent gases. For the use of SOG 14 to feed a COIL, the reaction chamber pressure is more preferably around 100 Torr to 400 Torr (0.13 atm to 0.52 atm). This pressure range for a COIL SOG also assists in the departure of the $O_2(^1\Delta)$ from the liquid solution, as compared to a significantly higher reactor pressure. These elevated pressures would result in collisional deactivation of the $O_2(^1\Delta)$ to the point where the gaseous stream no longer yields efficient laser action in prior art SOGs. Because of its compact, two-dimensional scalable configuration the SOG 14 according to the invention is preferably part of a plenum wall that directly feeds a converging/diverging nozzle of a laser. The $O_2(^1\Delta)$ generated in the BHP-chlorine reaction along the concave wall 30 need only travel a few centimeters, preferably about 10 cm (3.94 inches) or less, after departing the BHP-chlorine solution, which is preferably less than about 15 mm thick along concave wall 30, to reach the throat of the laser's nozzle 24 in the preferred embodiment. As seen in FIG. 2, nozzle throat 24 is preferably located opposite curved wall 30, such that the distance between curved wall 30 and nozzle throat 24 is less than about 10 cm or less. Consequently, $O_2(^1\Delta)$ vapor is at an elevated pressure for only a few milliseconds, and does not have time to collisionally deactivate to any significant extent. The reduction in contaminants in the $O_2(^1\Delta)$ stream and the close proximity of the SOG to the laser nozzle in the preferred embodiment of the invention make it feasible to produce $O_2(^1\Delta)$ at an elevated pressure.

A SOG according to a preferred embodiment of the invention yields $O_2(^1\Delta)$ at a higher rate than prior art SOGs. Due to deactivation while the $O_2(^1\Delta)$ is dissolved in the BHP solution, deactivation of walls and the dimol and pooling reactions for $O_2(^1\Delta)$, the yield of $O_2(^1\Delta)$ at the throat of a laser nozzle does not exceed about 50% in most prior art devices. Higher yield values are often cited for prior art devices, but these are upstream of the laser's nozzle throat. The dimol and pooling reactions are the dominant deactivation mechanisms and have driven prior art SOG systems to operate at low partial pressures for the $O_2(^1\Delta)$. However, according to the invention, deactivation of $O_2(^1\Delta)$ according to the other mechanisms is reduced. For instance, the $O_2(^1\Delta)$ rapidly departs the BHP solution inside the reaction chamber, there is no need for a water vapor trap, and the generated $O_2(^1\Delta)$ need only travel a short distance to the laser nozzle's throat. These factors allow a SOG according to the invention to operate at high pressures while still resulting in a yield as high as 70% or greater.

In addition to operation at a high pressure and with improved yield, the SOG according to the invention has a number of additional major advantages over prior art SOG devices. These include: (1) it is scalable, (2) it can operate in a zero-gravity or low gravity environment, (3) no added diluent or buffer gas is used, (4) the chemicals are efficiently utilized and (5) the $O_2(^1\Delta)$ stream is substantially free of chlorine and water vapor contamination.

Figure 3:
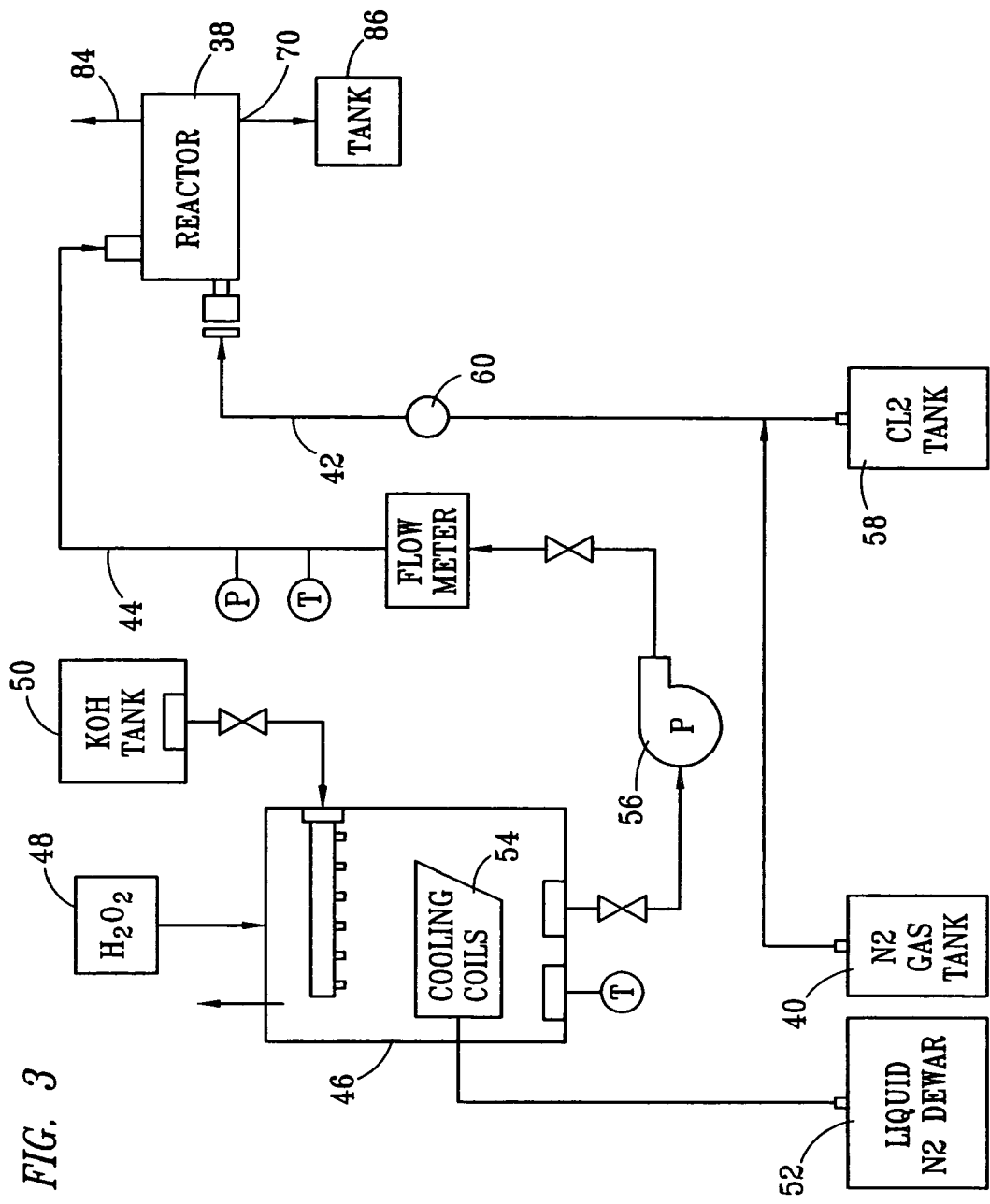
FIG. 3 is a schematic diagram of a SOG system, including BHP and chlorine feed systems, according to a feasibility experiment for the present invention.
Figure 4:
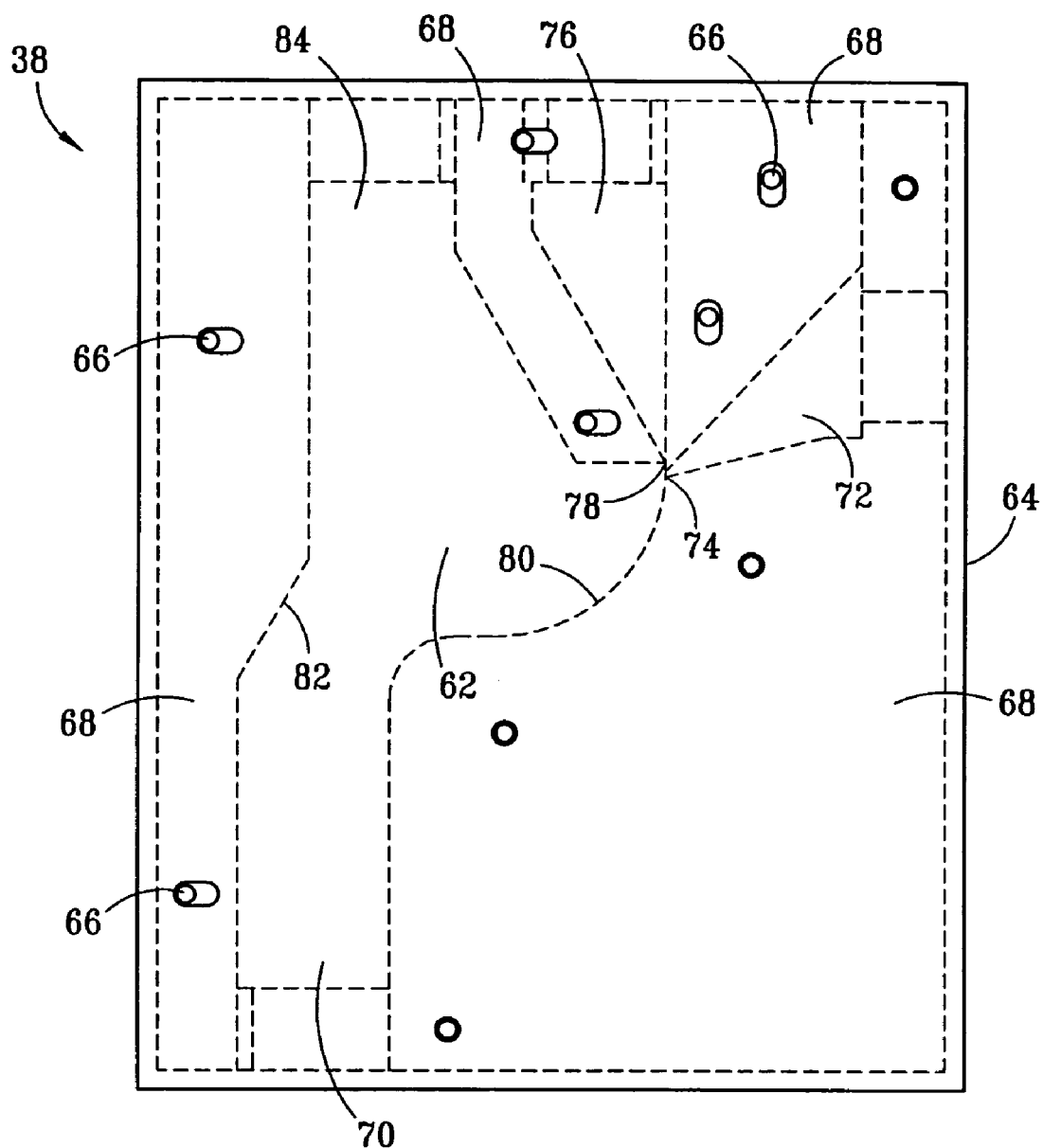
FIG. 4 is a cross-sectional side view of a reaction chamber of a SOG system according to a feasibility experiment for the present invention.

A SOG according to the invention was developed and tested in a feasibility experiment. A description of the test apparatus used in the feasibility experiment, and as depicted in FIGS. 3 and 4, and the results of the feasibility experiment are described below. Details regarding the amounts of reactants used, flow rates, part sizes, etc. described herein are illustrative of the preferred values for operation of a test-scale SOG in the feasibility experiment and do not limit the scope of the invention as claimed. Additionally, some details of the SOG and chemical supply systems and their methods of use in the feasibility experiment, including various gauges, fittings, piping, etc. are well known in the art, and as such are neither shown nor described.

FIG. 3 is a schematic diagram of a SOG system, including BHP and chlorine feed systems, according to a feasibility experiment for the present invention. The test apparatus consists of a BHP preparation system 46, a BHP feed system 56, a chlorine feed system 42, a SOG reactor 38, an exhaust system 84 for the generated $O_2(^1\Delta)$ gas, and an exhaust system 70 for the spent aqueous solution. The test materials are high-pressure nitrogen, a liquid nitrogen dewar, 30% aqueous $H_2O_2$, 45% aqueous KOH, liquid chlorine, distilled water, and tap water. All materials are commercially available.

Water/nitrogen preliminary flow tests are first performed with nitrogen replacing chlorine and water replacing BHP. High-pressure nitrogen from nitrogen gas tank 40 is used to purge chlorine line 42 and tap water flows through BHP line 44 to perform this preliminary flow test.

BHP is prepared in a batch by first pouring distilled water into mixer 46, after which an aqueous $H_2O_2$ solution is added from $H_2O_2$ tank 48. Aqueous KOH is then allowed to slowly drip into mixer 46 from KOH tank 50. Both the $H_2O_2$ and KOH solutions are pre-cooled in a refrigerator. During mixing with the KOH, the contents of mixer 46 are cooled with liquid nitrogen from nitrogen tank 52. Liquid nitrogen flows through a heat exchanger 54 with vertical copper tubing for the cold nitrogen. The BHP temperature is monitored during preparation, and the KOH drip rate is adjusted to avoid overheating the BHP solution.

After the BHP has been prepared, a positive displacement pump 56, in BHP line 44 between mixer 46 and SOG 38, pumps BHP to SOG 38. The liquid chlorine tank 58 includes an eductor tube, which provides liquid chlorine to a heater 60 that gasifies it. Chlorine vapor passes through line 42 to SOG 38. The time duration of a test is determined by the amount of BHP that has been prepared and the flow rate of BHP during a test run.

FIG. 4 is a cross-sectional side view of a SOG 38 and particularly reaction chamber 62 of SOG 38 according to a feasibility experiment for the present invention. Side walls 64 of SOG 38 are 0.25-inch thick, clear acrylic plates with a number of slotted holes 66 that allow for adjustment of four aluminum inserts 68 that provide flow paths for the BHP and chlorine reactants. The width of the inserts 68 is 1-inch, and the flow paths between side walls 64 are two-dimensional. The inlet and exhaust ducting, such as exhaust duct 70, is rectangular in cross-section, but the transition to a circular configuration is easily performed. Thus, the 1-in dimension is readily increased to any desired length; which establishes the scalability of a SOG according to the invention. The SOG 38 depicted in FIG. 4 is only slightly smaller than the actual test device. This verifies the compactness of a SOG according to the invention.

Chlorine vapor flows through a converging nozzle 72, entering reaction chamber 62 through a narrow two-dimensional slit, or throat 74. Although it is preferred to use a porous wall to inject the chlorine into the reaction chamber according to the invention, a nozzle configuration, as used in the feasibility experiment, may also be used. The BHP aqueous solution flows downward through a converging nozzle 76, entering reaction chamber 62 through a narrow, two-dimensional slit, or throat 78. The chlorine vapor enters reaction chamber 62 shortly after the BHP solution enters. The vapor and liquid mix and flow along a concave-curved wall 80. The reactant solution impacts an angled wall 82 that directs the liquid flow into an exhaust duct 70. A vapor exhaust 84, for exhausting $O_2(^1\Delta)$ gas, is located on the top side of SOG 38. The solution exiting through exhaust 70 flows to a collection tank 86 (as shown on FIG. 3). A 1.5 hp motor is located in the lid of the collection tank. The fan on the motor provides a small suction pressure that assists the flow of the spent liquid out of SOG 38.

In a feasibility experiment for a SOG according to the invention, the BHP solution comprises a mixture of about 1 gallon (3.79 L) of distilled water, 1 gallon (3.79 L) of 30% aqueous $H_2O_2$, and 0.8 gallons (3 L) of 45% aqueous KOH. These volumes translate into $H_2O_2$, KOH, and $H_2O$ molar ratios of approximately 1:1:10, where the $H_2O$ value includes the aqueous portions of the $H_2O_2$ and KOH solutions and the added water. In contrast to BHP solutions used in prior art SOGs, this BHP solution is dilute.

The $H_2O_2$ and KOH solutions are pre-cooled in a refrigerator to a temperature below 32° F. During BHP preparation, which took about 50 minutes during the feasibility experiment, the BHP temperature is limited to a maximum value of 36° F. The BHP is preferably cooled not only during its preparation, but further cooled, if necessary, to a temperature slightly above its freezing point before injection into the reactor. Anomalous freezing of the BHP solution that has been problematic in prior art systems does not occur according to the invention due to the use of a relatively dilute BHP solution, such as used in the feasibility experiment. A test run begins within a few minutes after BHP preparation is completed. For the feasibility experiment, positive displacement pump 56 is set for a BHP flow rate of about 1.7 gpm (6.4 L/min), which provided a run time of about 1.5 minutes.

The slit 78 at the exit of BHP nozzle 76 is about 0.02 inches (0.05 cm), while the slit 74 at the exit of chlorine nozzle 72 is about 0.06 inches (0.15 cm). Vapor exhaust 84 is throttled such that the vacuum pressure inside reaction chamber 62, during the test, is only about 6-inches of water, or 0.21 psi, below the ambient atmospheric pressure. This translates to a reaction chamber pressure of about 14.5 psi (750 Torr) without the use of any gaseous diluents, which is significantly higher than typical prior art systems.

The presence of $O_2(^1\Delta)$ in SOG 38 in the feasibility experiment described was confirmed by a visual inspection through the clear side walls of SOG 38. An intense red dimol emission confirmed that the reaction produced $O_2(^1\Delta)$. The emission was noted during the experiment immediately after the BHP and chlorine began mixing. This indicates the rapidity with which the reaction takes place.

In addition to the parameters of the feasibility experiment described above, nominal values for key parameters of a SOG according to the invention are as follows. These values are not considered to be minimums, maximums, or optimum values and may be adjusted according to the desired scale of the system. A 1 m (3.3 ft) depth for the SOG coupled with a radius of curvature for the concave wall of 2.5 cm (1 inch), a BHP nozzle throat of about 1 mm (0.04 in), a laser nozzle throat height of about 1.58 cm (0.62 in) and a laser nozzle exit height of about 9.8 cm (3.9 in). For a 1 m (3.3 ft) depth dimension, the chemical flow rates are:

| Constituent | Weight % of Aqueous Solution | Mass Flow Rate, kg/s (lb/s) |
|---|---|---|
| aq. $H_2O_2$ | 35 | 5.330 (11.751) |
| aq. KOH | 45 | 6.838 (15.075) |
| added $H_2O$ | — | 12.54 (27.65) |
| Chlorine | — | 1.75 (3.76) |

An improved SOG and its method of use are described according to the invention. It will be understood by those of skill in the art that variations in the components or arrangement of components described may be made within the scope of the invention.

The invention claimed is:

1. A singlet delta oxygen generator, comprising a chamber where at least a basic hydrogen peroxide (BHP) solution reacts with chlorine to produce singlet delta oxygen, wherein chlorine is introduced into the chamber through a porous inlet having pore diameters dimensioned to produce a frothy layer.

2. The generator of claim 1, wherein the chamber further comprises:
   an inlet for the BHP solution; and
   a curved wall over which the BHP and chlorine flow and react to produce singlet delta oxygen, byproducts, and a spent reactant solution.

3. The generator of claim 2, wherein the chamber further comprises:
   a singlet delta oxygen outlet; and
   a spent reactant outlet.

4. The generator of claim 3, wherein the singlet delta oxygen outlet comprises an inlet to a nozzle feeding a laser cavity.

5. The generator of claim 1, wherein the pressure in the generator is between about 100 Torr to about 760 Torr.

6. The generator of claim 1, wherein the generator further comprises a cooling system for cooling the BHP solution to a temperature between about 5° C. and about 10° C. above its freezing point prior to the inlet.

7. The generator of claim 1, wherein the chlorine molar flow rate is about 70-120% of the molar flow rate of the BHP solution.

8. A singlet delta oxygen generator, comprising:
   a cooler for cooling a BHP solution;
   a porous inlet having pore diameters dimensioned to produce a frothy layer, that introduces chlorine to the BHP solution; and
   a chamber that is downstream of the porous inlet, wherein reactants, including BHP solution and chlorine, pass through the chamber at a predetermined rate to produce a singlet delta oxygen stream having a reduced water vapor concentration.

9. The generator of claim 8, wherein the chamber further comprises:
   an inlet for the cooled BHP solution and chlorine; and
   a concave wall over which the cooled BHP solution and chlorine flow and react to produce singlet delta oxygen, byproducts, and a spent reactant solution.

10. The generator of claim 9, wherein the chamber further comprises:
    a singlet delta oxygen outlet; and
    a spent reactant outlet.

11. The generator of claim 10, wherein the singlet delta oxygen outlet comprises an inlet to a nozzle feeding a laser cavity.

12. A generator of claim 8, wherein the pressure in the generator is between about 100 Torr to about 760 Torr.

13. The generator of claim 8, wherein the cooler further comprises cooling the BHP solution to a temperature between about 5° C. and about 10° C. above its freezing point prior to the inlet.

14. The generator of claim 8, wherein the chlorine molar flow rate is about 70-120% of the molar flow rate of the cooled BHP solution.

* * * * *